(12) United States Patent
Burton et al.

(10) Patent No.: US 8,765,393 B2
(45) Date of Patent: Jul. 1, 2014

(54) ENDOTOXIN-BINDING LIGANDS AND THEIR USE

(75) Inventors: Steven James Burton, Cambridge (GB); Tadeusz Podgorski, Cambs (GB); Saji S. Eapen, Cambridge (GB)

(73) Assignee: Prometic Biosciences Ltd, Isle of Man (GB)

( * ) Notice: Subject to any disclaimer, the term of this patent is extended or adjusted under 35 U.S.C. 154(b) by 924 days.

(21) Appl. No.: 10/514,455

(22) PCT Filed: May 22, 2003

(86) PCT No.: PCT/GB03/02209
§ 371 (c)(1),
(2), (4) Date: Jun. 29, 2005

(87) PCT Pub. No.: WO03/097112
PCT Pub. Date: Nov. 27, 2003

(65) Prior Publication Data
US 2005/0238641 A1    Oct. 27, 2005

(30) Foreign Application Priority Data

May 22, 2002  (GB) .................................. 0211805.7

(51) Int. Cl.
*G01N 33/00* (2006.01)
*G01N 33/554* (2006.01)
*G01N 33/569* (2006.01)
*C12Q 1/00* (2006.01)

(52) U.S. Cl.
USPC ............... 435/7.32; 435/4; 435/6.15; 435/7.1; 435/7.94; 435/7.95; 435/32; 435/34; 435/38; 435/174; 435/181; 435/183; 435/287.1

(58) Field of Classification Search
None
See application file for complete search history.

(56) References Cited

U.S. PATENT DOCUMENTS 4,981,591 A * 1/1991 Ostreicher ................. 210/502.1

FOREIGN PATENT DOCUMENTS

| CA | 2249548 | | 9/1997 | |
|---|---|---|---|---|
| DE | 196 09 479 | A1 | 9/1997 | |
| EP | 0621074 | * | 4/1994 | ............ B01J 20/32 |
| EP | 107529 | * | 12/1999 | ............ B01J 20/26 |
| EP | 1 057 529 | A1 | 12/2000 | |
| WO | WO 91/04086 | A1 | 4/1991 | |
| WO | WO 9104086 | * | 4/1991 | ............ B01D 15/08 |
| WO | WO 97/33683 | * | 9/1997 | ............ B01D 69/02 |

OTHER PUBLICATIONS

Boden et al. 1995. J. of Immunol. Meth. vol. 181(2): 225-232.*

* cited by examiner

*Primary Examiner* — Ja'na Hines
(74) *Attorney, Agent, or Firm* — Saliwanchik, Lloyd & Eisenschenk

(57) ABSTRACT

An affinity ligand-matrix conjugate of the structure Z-Spacer-$[NX\text{-}A]_m\text{-}NY\text{-}A\text{-}NK_2$ is useful for the isolation, separation, purification, characterization, identification or quantification of endotoxins in an aqueous system, wherein m is an integer of at least one; each A independently represents an optionally substituted linear, branched or cyclic saturated hydrocarbon chain containing 1 to 6 carbon atoms; each X independently represents hydrogen or alkyl; Y is X or $A\text{-}NX_2$; and Z is a support matrix attached to the ligand through an optional spacer arm (Spacer).

11 Claims, No Drawings

ENDOTOXIN-BINDING LIGANDS AND THEIR USE

This application is a National Stage Application of International Application Number PCT/GB03/02209, filed May 22, 2003; which claims priority to United Kingdom application 0211805.7, filed May 22, 2002.

FIELD OF THE INVENTION

This invention relates to affinity ligands and to their use for the removal of endotoxins from a variety of fluids such as water, aqueous solutions, blood, plasma, pharmaceutical products, antibiotics, vaccines, proteins, nucleic acids and other biological products.

BACKGROUND OF THE INVENTION

Endotoxins are lipopolysaccharides (LPS) found in the outer membrane of gram-negative bacteria such as *E. coli* (Raetz, *Ann. Rev. Biochem.*, 1990, p. 129, Vol. 59). The LPS molecule contains three distinct chemical regions, the lipid A region, a central polysaccharide region and the O-antigen region. The lipid A region is composed of a glucosamine disaccharide containing phosphate groups and is highly substituted with long chain fatty acids and is thought to be responsible for the toxic effects of endotoxins (Rietschel et al, Cellular and Molecular Aspects of Endotoxin Reaction, Ed. Nowotny, A., Spitzner, J. J. and Ziegler, E. J., 1990, p. 15).

The biological effects induced by endotoxins result from activation of the immune system, especially the monocytes and macrophages, and are extremely diverse including fever, metabolic breakdown and septic shock (Martich et al, *Immunobiology*, 1993, p. 403, Vol. 187). The presence of endotoxins in biologically derived products and pharmaceutical products for therapeutic use is an area of major concern due to the potentially harmful effects of endotoxins. Although maintaining sterile processes can ensure that biological products are free from endotoxins, this is not often possible especially when the biological product is expressed in a gram-negative bacterial source such as *E. coli*. Typical processes for inactivating endotoxins include exposure to concentrated sodium hydroxide (1M NaOH) and/or heat treatment (250° C.) for prolonged periods of time. However, such treatment processes are not applicable to the majority of biological products.

Numerous techniques have been used to remove endotoxins from biological products and include ultrafiltration (Sweadner et al, *Appl. Environ. Microbiol.*, 1977, p. 382, Vol. 34; Li et al, *Biotechnol. Tech.*, 1998, p. 119, Vol. 12), charcoal adsorption (Nagaki et al, *Int. J. Artif. Organs.*, 1991, p. 43, Vol. 14), size exclusion chromatography, ion exchange chromatography (Hou et al, *J. Parenter. Sci. Technol.*, 1990, p. 204, Vol. 44; Hou et al, *Biotechnol. Bioeng.*, 1990, p. 315, Vol. 12; Neidhardt et al, *J. Chromatogr.*, 1992, p. 255, Vol. 590) and affinity chromatography. All these techniques exhibit significant drawbacks and especially when applied to endotoxin removal from therapeutic proteins and other biological products. Charcoal adsorption and ion exchange chromatography reduce endotoxin levels from protein solutions, but they also tend to bind the biological component.

Efficient endotoxin removal has been achieved using affinity chromatography on immobilized polymixin B (Talmadge et al, *J. Chromatogr.*, 1989, p. 175, Vol. 476; Anspach et al, *J. Chromatogr. A*, 1995, p. 81, Vol. 711). However, concerns over the potential toxicity of polymixin B leachates has limited its use. Synthetic ligands based on diaminoalkane and monoaminoalkane compounds attached to solid phase matrices have been used for the removal of endotoxins from aqueous solutions but have only shown a limited capacity for binding endotoxins (Hou et al, *Biochim. Biophys. Acta,* 1991, p. 149, Vol. 1073).

J. Chromatography 248, 401-408 (1982) and 262, 193-198 (1983), and also U.S. Pat. No. 4,381,239, describe histamine and other aromatic nitrogen heterocycles covalently linked to solid phase matrices.

U.S. Pat. No. 5,358,933 describes synthetic peptides for detoxification of bacterial endotoxin and for the prevention and treatment of septic shock.

SUMMARY OF THE INVENTION

This invention relates to the discovery of a novel class of synthetic affinity ligand structures for the selective capture and removal of endotoxin from solutions containing biological therapeutic products. Synthetic affinity ligand-matrix conjugates of the present invention may be described by the following generic structures (Structures 1 and 2):

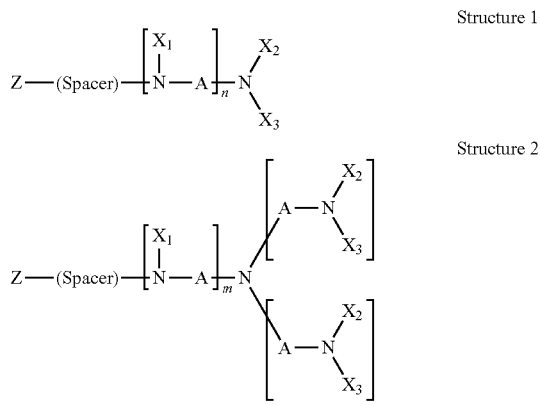

wherein A represents an optionally substituted linear, branched or cyclic saturated hydrocarbon chain, and each A in each repeating unit may be the same or different;

$X_1$, $X_2$ and $X_3$ each independently represent a hydrogen atom or an alkyl substituent;

n is 2 or more;

m is 1 or more; and the ligand is attached to a support matrix Z through an optional spacer arm.

Conjugates of Structure 2 in particular may be new.

DESCRIPTION OF PREFERRED EMBODIMENTS

Polyamine ligands having Structure 1 or 2 have at least 3 basic nitrogen atoms, and these nitrogen atoms are preferably separated from each other by at least two carbon atoms. The nitrogen atoms may be in the form of primary, secondary, tertiary or quaternary amine groups, and the intervening carbon atoms between pairs of nitrogen atoms may be in the form of a linear, branched or cyclic hydrocarbon chain.

By way of example, A may have the formula $-(CH_2)_x-CHR-(CH_2)_y-$ wherein x and y are independently 0, 1 or 2 and R is H or $C_{1-4}$ alkyl, e.g. hydrogen, methyl, ethyl, propyl or butyl. In particular, A may be a divalent $C_{1-4}$ alkyl radical, i.e. methyl, ethyl, n-propyl, isopropyl, n-butyl, isobutyl, secbutyl or tert-butyl, or 1,4-cyclohexylene, e.g. derived from trans-1,4-diaminocyclohexane. More generally, A may have up to 6 or 10 C atoms.

m and n are each preferably 1, 2, 3 or 4. X may have up to 6 or 10 C atoms.

The support matrix Z may be any compound or material, particulate or non-particulate, soluble or insoluble, porous or non-porous, which may be used for the immobilization of endotoxin affinity ligands to form an endotoxin ligand-matrix conjugate, thereby providing a convenient means of removing endotoxins from a contacting solution. Examples of particulate support matrices include natural polymers such as agarose, dextran, cellulose or starch, synthetic polymers and co-polymers such as polystyrene, polyacrylamide, polyvinyl alcohol, perfluorocarbons and polymethylmethacrylate, and inorganic compounds such as silica, glass, alumina and metal oxides. Examples of soluble carriers include polymers of dextran, polyvinyl alcohol, polyethylene glycol and hydrolysed starch. The support matrix may also be in the form of membranes or sheets comprising the above polymers and other polymers such as nitrocellulose, polyethersulphone and nylon.

Covalent attachment of ligands to the support matrix Z may be achieved by use of a variety of activation agents including but not limited to cyanogen bromide, epichlorohydrin, 1,4-butanediol diglycidyl ether, 1,2,7,8-diepoxyoctane, tosyl chloride, tresyl chloride, divinyl sulphone and cyanuric chloride.

The spacer arm may be absent If present, it may be introduced as part of the activation procedure, and is preferably represented by the structure

-T-L- where T represents an oxygen atom, a sulphur atom or a group N—$R_2$ wherein $R_2$ represents a hydrogen atom or an alkyl group containing 1 to 6 carbon atoms; and L is an optionally substituted alkyl, alkyl ether, alkyl thioether, alkyl ester or amide linkage containing from 2 to 20 carbon atoms.

Particularly preferred conjugates according to the present invention include:

Z-(Spacer)-NH(CH$_2$)$_2$N[(CH$_2$)$_2$NH$_2$]$_2$     (A)

Z-(Spacer)-NH(CH$_2$)$_2$NH(CH$_2$)$_2$NH$_2$     (B)

Z-(Spacer)-NH(CH$_2$)$_2$NH(CH$_2$)$_2$NH(CH$_2$)$_2$NH$_2$     (C)

Z-(Spacer)-NH(CH$_2$)$_2$NH(CH$_2$)$_3$NH$_2$     (D)

Z-(Spacer)-NH(CH$_2$)$_3$NH(CH$_2$)$_3$NH(CH$_2$)$_3$NH$_2$     (E)

Z-(Spacer)-NH(CH$_2$)$_3$NH(CH$_2$)$_2$NH(CH$_2$)$_3$NH$_2$     (F)

Z-(Spacer)-NH(CH$_2$)$_2$N[(CH$_2$)$_3$NH$_2$]$_2$     (G)

where Z and (Spacer) have the same meanings as described earlier.

In one embodiment of the invention, affinity conjugates of the invention may be conveniently prepared by covalent coupling of an appropriate polyamine to a pre-activated water-insoluble matrix. For example, coupling of polyamine ligand (A) to an epichlorohydrin-activated agarose matrix may be achieved according to the reaction scheme shown below (Scheme 1):

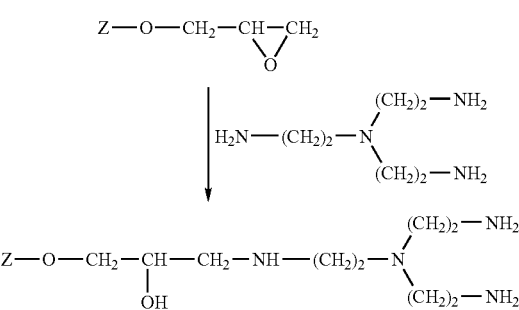

Scheme 1

The intervening group between Z and the polyamine ligand forms a spacer arm.

According to a preferred aspect of this invention, a process for the capture and removal of endotoxin from a solution containing endotoxin comprises contacting an affinity conjugate as defined above with the solution, preferably at a pH in the range 1.0 to 13.0. Examples of such solutions include fluids such as water, aqueous solutions, blood, plasma, pharmaceutical products, antibiotics, proteins, nucleic acids and other biological products. Another use of the endotoxin-binding ligand-matrix conjugates of the invention is for the extracorporeal removal of endotoxin from whole blood or plasma. The endotoxin-binding ligand-matrix conjugate may be conveniently used by packing the conjugate in a column and passing the endotoxin-contaminated solution through the column using gravity or other mechanical means. Alternatively, the conjugate may be mixed with an endotoxin-containing solution and used in a batch-wise manner.

In another embodiment of this invention, the conjugate may be attached to a porous membrane and used as a single-use disposable filtration device for the selective removal of endotoxin from solution.

In yet another embodiment of this invention, endotoxin-binding ligands of the invention may be attached to a soluble polymeric or non-polymeric carrier such as dextran, polyvinyl alcohol, polyethylene glycol or hydrolysed starch, e.g. for the in vivo capture and detoxification of endotoxin.

Conjugates of the present invention have been found to be highly efficient and selective at removing endotoxin from buffered and non-buffered solutions of antibiotics and proteins whilst demonstrating a low selectivity for the biological component.

The following Examples illustrate the invention. Examples 1 to 3 show the preparation of conjugates, and Examples 4 to 6 their use in endotoxin removal.

Example 1

Stage 1—Preparation of Epichlorohydrin-Activated PuraBead® 6XL

A slurry of preservative-free PuraBead® 6XL (200 g settled weight), RO water (128 ml) and 10 M sodium hydroxide (3.2 ml) was reacted with epichlorohydrin (14.4 ml) at 40° C. for 1 hour. The epoxy-activated PuraBead® 6XL was washed exhaustively with RO water (10×200 ml aliquots) to remove excess reactants and used immediately in stage 2.

Stage 2—Preparation of tris(2-aminoethyl)amine—PuraBead® 6XL

Epoxy-activated PuraBead® 6XL (200 g settled weight) from stage 1 was added in aliquots to an aqueous solution of tris(2-aminoethyl)amine (15.97 g in 80 ml RO water) and the reaction mixture stirred for 16 hours at 40° C. The resulting aminated adsorbent was washed with RO water (10×200 ml aliquots) and stored in 20% (v/v) aqueous ethanol till further use.

Example 2

Stage 1—Preparation of Epichlorohydrin-Activated PuraBead® 6XL

A slurry of preservative-free PuraBead® 6XL (200 g settled weight), RO water (128 ml) and 10 M sodium hydroxide (3.2 ml) was reacted with epichlorohydrin (14.4 ml) at 40° C. for 1 hour. The epoxide-activated PuraBead® 6XL was washed exhaustively with RO water (10×200 ml aliquots) and used immediately in stage 2.

Stage 2—Preparation of Triethylenetetraamine-PuraBead® 6XL

The epoxy-activated PuraBead® 6XL (200 g settled weight) from stage 1 was added in aliquots to an aqueous solution of triethylenetetraamine (8.04 g in 60 ml RO water) and the resulting slurry stirred for 16 hours at 40° C. The aminated adsorbent was washed with copious amounts of RO water (10×200 ml portions) to remove excess polyamine.

Example 3

Purabead 6XL was washed with 10 bed volumes of RO water and 300 g of drained gel slurried with 192 ml RO water. 10 M NaOH (4.8 ml) was added and the mixture warmed to 36° C. whereupon 21.6 ml epichlorohydrin was added. The reaction temperature was increased to 40° C. and maintained at this temperature for 1 hour, after which the activated Purabead was washed with 10 bed volumes of RO water and allowed to drain under gravity. N,N'-Bis(3-aminopropyl)ethylenediamine (9.586 g) in 60 ml water was added and the mixture heated to 40° C. to which 100 g epoxy activated agarose was added in portions over a period of 30 minutes. The reaction slurry was stirred for 16 hours at 40° C. and washed with 10 bed volumes water to remove excess amine.

Example 4

Depyrogenated conjugates (1 ml) prepared according to Examples 1-3 (Conjugates A, C and G) were added to an aqueous solution of gentamicin (2 ml, 9 mg/ml) containing *Escherichia coli* #0113:H10:K negative endotoxin ($1.0 \times 10^3$ EU) and the resulting slurry was agitated for 1 hour at 25° C. The supernatant was assayed for the presence of endotoxin using the Limulus Amoebocyte Lysate Turbidimetric assay (see Table 1).

TABLE 1

| Conjugate | Total EU Load | Unbound Endotoxin | % Endotoxin Bound | % Gentamicin Recovered |
|---|---|---|---|---|
| A | 1005.8 EU | 0.49 EU | 99.95 | 100 |
| C | 1005.8 EU | 1.09 EU | 99.89 | 100 |
| G | 815.1 EU | 0.77 EU | 99.91 | 100 |

The results indicate extremely efficient and selective removal of endotoxin from aqueous solutions of gentamicin sulphate with 100% recovery of gentamicin.

Example 5

Depyrogenated conjugate (Conjugate A, 1 ml) was added to a buffered (150 mM phosphate buffered saline, pH 7.4) solution of human serum albumin (2 ml, 27 mg/ml) containing *Escherichia coli* #0113:H10:K negative endotoxin ($3.0 \times 10^2$ EU) and agitated for 1 hour at 25° C. The supernatant was assayed for unbound endotoxin using the Limulus Amoebocyte Lysate Turbidimetric assay which was calibrated to detect endotoxin in the appropriate concentration of human serum albumin. The results are shown in Table 2.

TABLE 2

| Conjugate | Total EU Load | Unbound Endotoxin | % Endotoxin Bound | % Albumin Recovered |
|---|---|---|---|---|
| A | 308.9 EU | 2.23 EU | 99.3 | 100 |

The results demonstrate greater than 99% removal of endotoxin in the presence of human serum albumin whilst maintaining 100% recovery of the applied protein.

Example 6

Depyrogenated conjugates (Conjugates A and C, 1 ml) prepared according to Examples 1 and 2, respectively, were packed into a glass column (10 mm i.d.×30 mm height) and equilibrated with 20 ml endotoxin-free water. A solution of gentamicin sulphate in water (1 ml, 3 mg/ml) containing *Escherichia coli* #0113:H10:K negative endotoxin ($7.5 \times 10^2$ EU) was loaded onto to column at a linear flow rate of 61 cm/hr. The column was then washed with endotoxin-free water (9 ml) to remove any unbound endotoxin and the combined flow through assayed for endotoxin content using the Limulus Amoebocyte Lysate assay. The results are shown in Table 3.

TABLE 3

| Conjugate | Total EU Load | Unbound Endotoxin | % Endotoxin Bound | % Gentamicin Recovered |
|---|---|---|---|---|
| A | 774.8 EU | 0 EU | 100 | 100 |
| C | 926.1 EU | 4.87 EU | 99.5 | 95.2 |

The invention claimed is:
1. A method of selective removal of endotoxins from an aqueous system comprising one or more antibiotics and/or proteins wherein said method comprises the use of an affinity ligand-matrix conjugate of the structure

Z-Spacer-Ligand wherein the ligand is tris(2-aminoethyl)amine;
wherein the ligand is attached to a support matrix Z through the spacer,
wherein said endotoxins are lipopolysaccharides (LPS) from gram-negative bacteria,
and wherein the method comprises:
contacting the affinity ligand-matrix conjugate with the aqueous system under conditions such that endotoxins in the aqueous system bind directly to the ligand, and
recovering the aqueous system that has been contacted with the affinity ligand matrix conjugate and from which endotoxins have been removed; wherein essentially all of the protein and/or antibiotic remains in the aqueous system.

2. The method according to claim 1, wherein Z is selected from porous agarose beads, perfluorocarbon particles and functionalized membranes.

3. The method according to claim 1, wherein the aqueous system has a pH in the range of 3 to 10.

4. The method according to claim 1, wherein the aqueous system is contacted with a suspension or packed bed of the conjugate.

5. The method according to claim 1, wherein the aqueous system comprises whole blood or plasma and wherein the method comprises passing the aqueous system through an extracorporeal device comprising said affinity ligand-matrix conjugate under conditions such that endotoxins in the aqueous system bind directly to the ligand and are thereby removed from the aqueous system.

6. The method according to claim 1, wherein the ligand is attached to a soluble polymeric or non-polymeric carrier for in vivo capture of endotoxin.

7. The method according to claim 1, comprising providing an aqueous system comprising one or more antibiotics, wherein the recovered aqueous system comprises said one or more antibiotics.

8. The method according to claim 1, wherein Z is a porous agarose bead.

9. The method according to claim 1, wherein Z is a perfluorocarbon particle.

10. The method according to claim 1, wherein Z is a functionalized membrane.

11. The method according to claim 1, wherein at least 99% of the endotoxin is removed from the aqueous system.

* * * * *